(12) United States Patent
Tamura et al.

(10) Patent No.: US 10,139,334 B2
(45) Date of Patent: Nov. 27, 2018

(54) PARTICULATE MEASUREMENT DEVICE

(71) Applicant: TOKYO ELECTRON LIMITED, Tokyo (JP)

(72) Inventors: Akitake Tamura, Tokyo (JP); Kaoru Fujihara, Nirasaki (JP)

(73) Assignee: TOKYO ELECTRON LIMITED, Tokyo (JP)

( * ) Notice: Subject to any disclaimer, the term of this patent is extended or adjusted under 35 U.S.C. 154(b) by 0 days.

(21) Appl. No.: 15/560,891

(22) PCT Filed: Mar. 17, 2016

(86) PCT No.: PCT/JP2016/058473
§ 371 (c)(1),
(2) Date: Sep. 22, 2017

(87) PCT Pub. No.: WO2016/158443
PCT Pub. Date: Oct. 6, 2016

(65) Prior Publication Data
US 2018/0120216 A1 May 3, 2018

(30) Foreign Application Priority Data
Mar. 27, 2015 (JP) .................. 2015-065965

(51) Int. Cl.
*G01B 11/14* (2006.01)
*G01N 15/14* (2006.01)
*G01N 15/00* (2006.01)

(52) U.S. Cl.
CPC ..... *G01N 15/1436* (2013.01); *G01N 15/1404* (2013.01); *G01N 15/1459* (2013.01); *G01N 2015/0053* (2013.01)

(58) Field of Classification Search
CPC ..... G01B 11/026; G01B 11/002; G01B 11/14; G01S 5/163; G01S 5/16
(Continued)

(56) References Cited

U.S. PATENT DOCUMENTS

| 5,530,540 A | 6/1996 | Wyatt et al. |
| 8,691,584 B2 * | 4/2014 | Durack .................. G01N 33/48 422/73 |

(Continued)

FOREIGN PATENT DOCUMENTS

| JP | S60-243565 A | 12/1985 |
| JP | 64018046 A * | 7/1987 |

(Continued)

OTHER PUBLICATIONS

International Search Report issued in PCT/JP2016/058473; dated May 24, 2016.

(Continued)

*Primary Examiner* — Md M Rahman
(74) *Attorney, Agent, or Firm* — Studebaker & Brackett PC

(57) ABSTRACT

A particulate measurement device includes: a nozzle which discharges liquid from an opening to form a flow of the liquid; a light emitter which emits light such that the light propagates in a region where the flow of the liquid is formed; a photodetector provided outside the region to receive the light from a partial region extending along a longitudinal direction of the region; and an air flow forming unit which forms a flow of gas along a direction in which the liquid flows, on an outer periphery of the region.

7 Claims, 3 Drawing Sheets

(58) Field of Classification Search
USPC .......................................................... 356/614
See application file for complete search history.

(56) References Cited

U.S. PATENT DOCUMENTS

| 2002/0145711 | A1* | 10/2002 | Magome | ............. | G03F 7/70858 |
| | | | | | 355/30 |
| 2012/0257192 | A1* | 10/2012 | Jiang | .................. | G01N 21/6486 |
| | | | | | 356/73 |
| 2013/0224734 | A1* | 8/2013 | Durack | ................ | C12N 5/0612 |
| | | | | | 435/6.1 |
| 2017/0336312 | A1* | 11/2017 | Stoeber | .................. | G01N 15/06 |

FOREIGN PATENT DOCUMENTS

| JP | S64-018046 A | 1/1989 |
| JP | H04-198738 A | 7/1992 |
| JP | H06-011433 A | 1/1994 |

OTHER PUBLICATIONS

"Submerged Particle Measurement", RION Co., Ltd., Measurement Technology Department, http://www.rion.co.jp/product/docs/07.pdf, Oct. 2007, pp. 1-4.

\* cited by examiner

PARTICULATE MEASUREMENT DEVICE

TECHNICAL FIELD

Embodiments of the present invention relate to a particulate measurement device.

BACKGROUND ART

A particulate measurement device is used in order to measure the number of particulates in liquid. Patent Literature 1 and Non-Patent Literature 1 disclose, as one type of a particulate measurement device, a device which performs detection of particles by making liquid flow into a transparent cell such as quartz and observing scattered light which is generated when the cell is irradiated with light.

Further, Patent Literature 2 discloses a counter which counts the number of bacteria by irradiating sample water containing fluorescently stained bacteria with excitation light and receiving fluorescence from the bacteria. In this counter, a jet stream is formed by the sample water discharged from a nozzle. Then, the jet stream is irradiated with light from an excitation light source, and fluorescence from within a water flow is received by a photodetector. The number of bacteria is determined based on a signal which is output from the photodetector.

CITATION LIST

Patent Literature

[Patent Literature 1] Japanese Patent Application Laid-Open Publication No. H6-11433
[Patent Literature 2] Japanese Patent Application Laid-Open Publication No. S64-18046

Non Patent Literature

[Non-Patent Literature 1] "Particle measurement in liquid" [online], October 2007, Rion Co., Ltd. [Search on Mar. 20, 2015], Internet <URL:http://www.rion.co.jp/product/docs/07.pdf>

SUMMARY OF THE INVENTION

Technical Problem

Generally, in a particulate measurement device, in order to perform measurement of particulates with a higher degree of accuracy, it is required to improve the ratio of a signal based on light from the particulate to noise based on the other light, that is, an SN ratio. As one method of improving the SN ratio, it is conceivable to increase a signal by lengthening a section (a measurement region) of a water flow, in which the particulates are measured. However, in a case of performing observation by making liquid flow into a cell, as in Patent Literature 1 and Non-Patent Literature 1, scattered light is generated at the surface of the cell or the interface between the cell and the liquid. Since such scattered light becomes stray light, there is a problem in that noise increases.

Further, in the counter of Patent Literature 2, a method without a cell is used. However, if the length of the jet stream discharged from the nozzle becomes greater than or equal to a certain length, the jet stream enters a turbulent state where the water flow is unstable. If a region where the water flow is unstable in this manner is included in a measurement region, light which causes noise may be generated from the surface of the water flow or the like and the SN ratio may decrease. Therefore, the region where the water flow is unstable cannot be used as the measurement region, and thus it is difficult to lengthen the measurement region. From such a background, a particulate measurement device capable of forming a stable liquid flow over a long section is required.

Solution to Problem

In one aspect, a particulate measurement device is provided. The particulate measurement device includes a nozzle, a light emitter, a photodetector, and an air flow forming unit. The nozzle discharges liquid from an opening to form a flow of the liquid. The light emitter emits light such that the light propagates in a region where the flow of the liquid is formed. The photodetector is provided outside the region to receive the light from a partial region extending along a longitudinal direction of the region. The air flow forming unit forms a flow of gas along a direction in which the liquid flows, on an outer periphery of the region.

In the particulate measurement device according to the one aspect, the air flow forming unit forms, around the flow of the liquid (a liquid flow) from the nozzle, the flow of the gas (an air flow) along the direction of the liquid flow. The air flow enables a stable substantially columnar liquid flow to be formed over a long section. The light from a partial region of the region where the liquid flow is formed is received by the photodetector, and therefore, it is possible to obtain a signal with a high SN ratio based on light from particulates passing through the partial region.

In one embodiment, the air flow forming unit may have an adjustment function for adjusting a speed of the air flow. According to this embodiment, the speed of the air flow is adjusted according to the speed of the liquid flow which is discharged from the nozzle. Therefore, a more stable substantially columnar liquid flow is formed.

In one embodiment, the light emitter may emit light from an inside of the nozzle through the opening, and a shielding portion which blocks light may be provided between the opening and the photodetector. According to this embodiment, stray light from the opening is prevented from reaching the photodetector. Therefore, noise is reduced.

In one embodiment, the air flow forming unit may configure the shielding portion. According to this embodiment, a separate component for light shielding is unnecessary.

In one embodiment, the light emitter may have a condensing optical element which narrows a beam width of the light in the opening to be smaller than the opening. According to this embodiment, noise light which is generated due to the light from the light emitter being reflected or scattered at a peripheral edge of the opening is suppressed. Further, the light condensed by the condensing optical element spreads in the liquid flow, and therefore, the light propagates in a wide range in the liquid flow.

In one embodiment, the particulate measurement device may further include: a recovery part having a recovery port for recovering the liquid; and another air flow forming unit which forms a flow of gas along a direction in which the liquid flows, on a side of the recovery port with respect to the partial region and on an outer periphery of the region. According to this embodiment, it is possible to stabilize the liquid flow on the side of the recovery port with respect to the partial region. Therefore, noise light which is generated from the side of the recovery port with respect to the partial region can be reduced.

In one embodiment, the particulate measurement device may further include an optically transparent tubular member provided to surround the partial region through a region where the flow of the gas is formed. According to this embodiment, the air flow around the partial region where the photodetector performs observation is stabilized.

Advantageous Effects of Invention

As described above, it is possible to stabilize the water flow and perform the measurement of the particulates in the water flow with a high degree of accuracy.

DESCRIPTION OF EMBODIMENTS

Hereinafter, embodiments according to the present invention will be specifically described with reference to the drawings. For the sake of convenience, substantially the same elements may be denoted by the same reference symbols, and description thereof may be omitted.

First Embodiment

Figure 1:
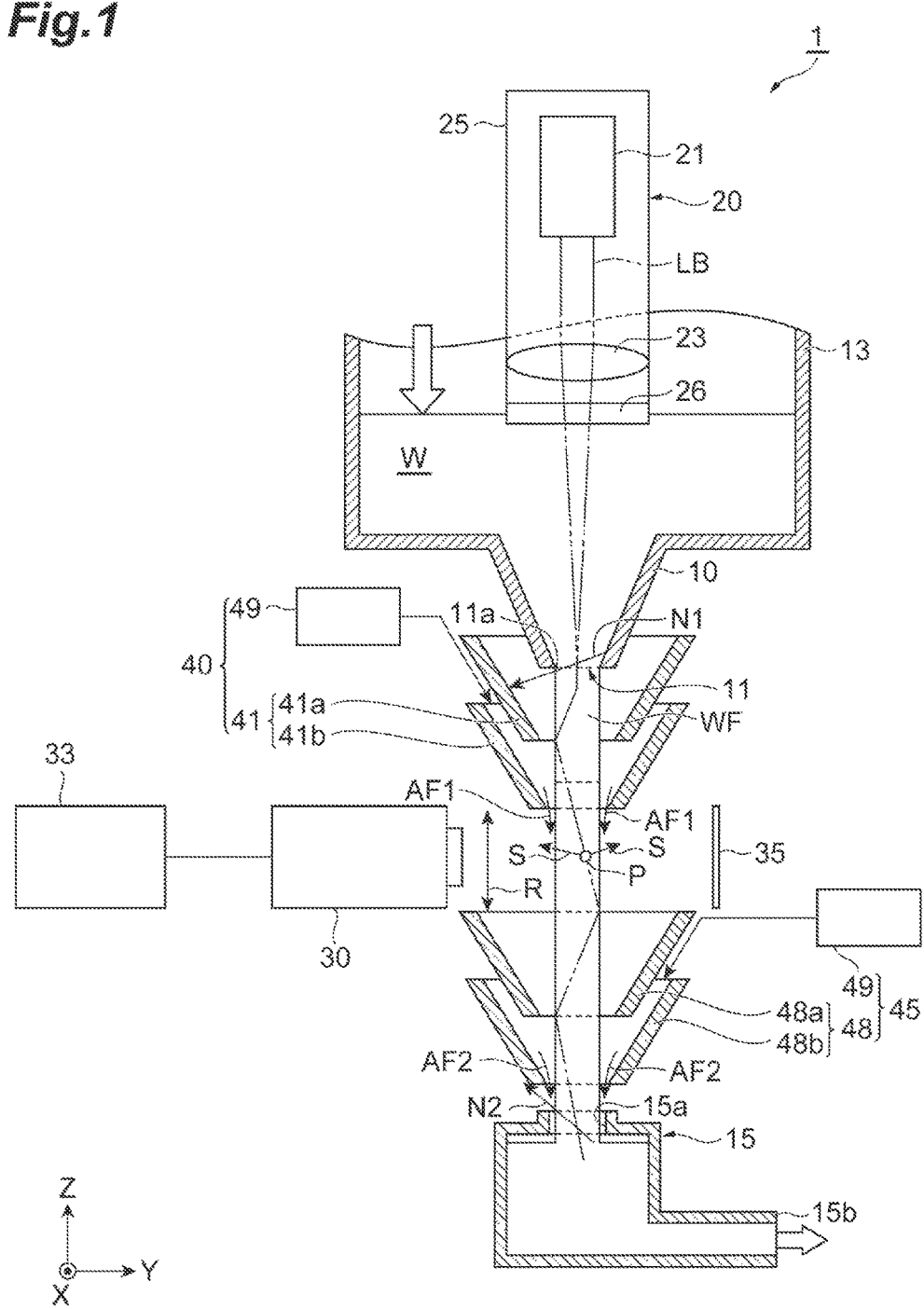
FIG. 1 is a sectional view schematically showing a particulate measurement device according to a first embodiment.

FIG. 1 is a sectional view schematically showing a particulate measurement device. A particulate measurement device 1 shown in FIG. 1 is a device which measures particulates included in any liquid, and is, for example, a device which measures the number of particulates included in ultrapure water which is used for cleaning of, for example, a semiconductor, with dark-field illumination. The particulate measurement device 1 is provided with a nozzle 10, a light emitter 20, a photodetector 30, and an air flow forming unit 40.

The nozzle 10 discharges liquid to form a substantially columnar liquid flow (a liquid flow). In an example, the nozzle 10 forms a liquid flow heading vertically downward. Hereinafter, an example in which the nozzle 10 discharges water W as the liquid will be described. However, the liquid which is discharged by the nozzle 10 may be any liquid. In one embodiment, the nozzle 10 is connected to a reservoir 13 at one end thereof. The reservoir 13 is configured to store the water W which is supplied thereto. For example, the reservoir 13 can have a bottomed cylindrical shape which provides an internal space in which the water W is stored. The nozzle 10 is connected to the center of the bottom surface of the reservoir 13 to communicate with the internal space of the reservoir 13. The nozzle 10 has a tubular shape which decreases in diameter as it approaches an opening end 11a provided on the lower end side thereof. The opening end 11a of the nozzle 10 defines an opening 11. The nozzle 10 discharges the water W from the opening 11 such that the water W forms a substantially columnar water flow WF having no disturbance on the surface and inside thereof. The term, a substantially columnar shape, does not mean a strictly columnar body shape, but includes the shape of a substantially columnar body which decreases in diameter as it goes downward. In one embodiment, the water W is discharged from the nozzle 10 by pressure due to its own weight stored in the reservoir 13 and falls freely. In this case, the amount of the water W stored in the reservoir 13 may be adjusted to be constant by a water amount adjuster (not shown). Accordingly, the discharge pressure of the water W becomes always constant. The discharge pressure of the water W may be adjusted by adjusting the pressure of gas (for example, the air or an inert gas) in the reservoir 13.

A recovery part 15 is disposed below the nozzle 10. The recovery part 15 is for recovering the water W discharged from the opening 11. A recovery port 15a is formed in the recovery part 15. The recovery port 15a is formed in an upper portion of the recovery part 15 and below the opening 11 of the nozzle 10. The water W discharged from the nozzle 10 is recovered in the recovery part 15 through the recovery port 15a. The recovery part 15 is provided with a drainage port 15b for discharging the recovered water W.

The light emitter 20 is disposed inside the nozzle 10 with respect to the opening 11 and emits light LB such that the light LB propagates in a substantially columnar region where the water flow WF is formed, on the same principle as an optical fiber. That is, in general, the refractive index of liquid is larger than the refractive index of air, and therefore, the light propagating in the liquid has a critical angle which causes total reflection at a gas-liquid interface. For this reason, depending on the incidence angle of the light LB on the water flow WF, the light LB propagates while repeating total reflection at the gas-liquid interface. In one embodiment, the light emitter 20 is provided with a light source 21 and a condensing lens (a condensing optical element) 23. The light source 21 is, for example, a laser light source and is disposed to emit the light LB toward the opening 11. The condensing lens 23 is disposed between the light source 21 and the opening 11. The condensing lens 23 condenses the light LB emitted from the light source 21 and narrows the beam width of the light LB in the opening 11 to be smaller than the width of the opening 11. Accordingly, the light LB emitted from the light source 21 passes through the inside of the opening 11 without hitting against the opening end 11a.

The light source 21 and the condensing lens 23 are accommodated in a casing 25. The casing 25 is a tubular body having at least a bottom surface formed on the side on which the light LB is emitted. The bottom surface is an emission port 26 through which the light emitted from the light source 21 penetrates, and is formed of an optically transparent material such as quartz glass, for example. The casing 25 is disposed such that the emission port 26 is immersed in the water W in a state where water is stored in the reservoir 13 of the nozzle 10. Therefore, the light emitted from the light emitter 20 is propagated directly from the emission port 26 into the water, and therefore, generation of scattered light can be reduced.

The photodetector 30 is for detecting the light from a partial region (a measurement region R) along a longitudinal direction of a substantially columnar region where the water flow WF is formed, and is disposed outside the substantially columnar region. Further, the photodetector 30 is directed to the measurement region R to receive the light from the direction intersecting the direction of the water flow WF. For the photodetector 30, for example, a light receiving element such as a CCD or a CMOS can be used. The photodetector 30 is connected to a processing unit 33. The processing unit 33 analyzes a signal detected by the photodetector 30. For example, the photodetector 30 outputs a signal having a signal level corresponding to the detected light amount to the processing unit 33. Then, the processing unit 33 counts the number of pulses having a signal level higher than or equal to a predetermined threshold value in the signal input from the photodetector 30, as the number of particulates (the particulate number) included in the water W.

Figure 2:
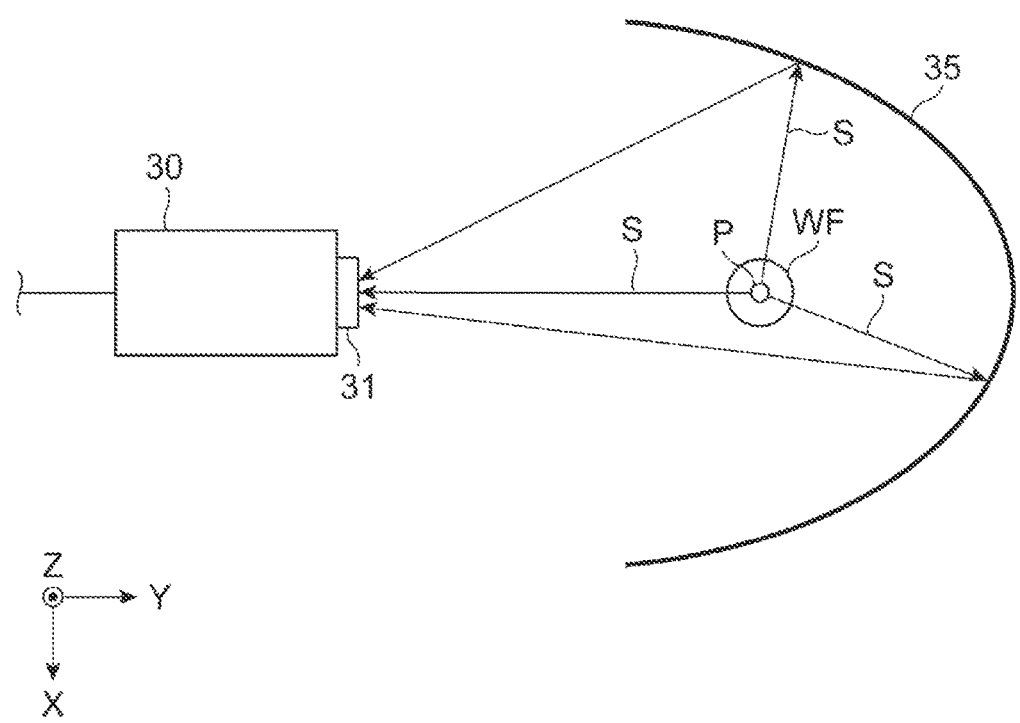
FIG. 2 is a diagram for describing a detector of the particulate measurement device of FIG. 1.

FIG. 2 is a schematic diagram for describing the photodetector 30 and shows the arrangement of the photodetector 30, the water flow WF, and a mirror 35 in an X-Y plane of FIG. 1. The photodetector 30 has a light receiver 31 on which the light LB is incident. In one embodiment, the mirror 35 is disposed in front of the light receiver 31 to face the light receiver 31. The substantially columnar region where the water flow WF is formed is located between the light receiver 31 and the mirror 35. The mirror 35 provides a reflecting surface having a curved surface shape extending along the surface of an elliptic cylinder extending in a Z-axis direction. One focal point of the mirror 35 is substantially at the center of the water flow WF in the X-Y plane, and another focal point is aligned with the light receiver 31 of the photodetector 30. In this embodiment, scattered light S from the particulate P in the water flow WF advances to the mirror 35 side and is reflected toward the light receiver 31 by the mirror 35. Therefore, the amount of light which is received by the light receiver 31 increases. In this manner, the shape of the mirror 35, the aperture of the light receiver 31, and the like are set such that the scattered light S from the particulate P in the water flow WF is incident on the light receiver 31.

FIG. 1 is referred to again. The air flow forming unit 40 forms an air flow AF1 for stabilizing the substantially columnar water flow WF in the measurement region R. In one embodiment, the air flow forming unit 40 has a gas guide section 41 and a blower 49. The blower 49 is connected to the gas guide section 41 and supplies gas, for example, air, to the gas guide section 41. The gas guide section 41 guides the gas supplied from the blower 49, and discharges the gas from a discharge port thereof, thereby forming the air flow AF1 around the substantially columnar region where the substantially columnar water flow WF is formed. In one embodiment, the gas guide section 41 has a tubular body 41a and a tubular body 41b. Each of the tubular body 41a and the tubular body 41b has a tubular shape which decreases in diameter as it approaches an end portion on the lower side thereof. The tubular body 41a and the tubular body 41b are coaxially disposed around the substantially columnar region where the water flow WF is formed. The gap between the tubular body 41a and the tubular body 41b which are disposed in this manner functions as a gas flow path. Further, lower ends of the tubular body 41a and the tubular body 41b configure gas discharge ports in the gas guide section 41, and are disposed below the nozzle 10 and above the measurement region R. The inner diameter of the lower end of the tubular body 41b disposed on the outside is formed to be smaller than the inner diameter of the lower end of the tubular body 41a disposed on the inside. Accordingly, the air flow AF1 can be efficiently blown to the water flow WF.

If gas is supplied from the blower 49 to the gas guide section 41, the gas is discharged from the discharge port of the gas guide section 41 through the gap between the tubular body 41a and the tubular body 41b. In this way, the air flow forming unit 40 forms the air flow AF1 downward along the water flow WF, along the outer periphery of the substantially columnar region where the water flow WF is formed. In one embodiment, the air flow forming unit 40 has an adjustment function for adjusting the speed of the air flow AF1. For example, the air flow forming unit 40 can arbitrarily adjust the speed of the air flow AF1 by adjusting the output of the blower 49.

Further, in one embodiment, the tubular body 41a and the tubular body 41b, that is, the gas guide section 41, of the air flow forming unit 40 has a light shielding property and configures a shielding portion. The shielding portion is interposed between the opening 11 and the photodetector 30 and blocks light such that noise light N1 which is generated at the opening 11 does not reach the photodetector 30.

Further, in one embodiment, another air flow forming unit 45 is disposed on a side of the recovery port 15a with respect to the measurement region R. The air flow forming unit 45 forms an air flow AF2 for stabilizing the substantially columnar water flow WF on the side of the recovery port 15a with respect to the measurement region R. The air flow forming unit 45 has the same configuration as that of the air flow forming unit 40 and has a gas guide section 48 having a tubular body 48a and a tubular body 48b, and a blower 49 connected to the gas guide section 48. The air flow forming unit 45 forms the air flow AF2 downward along the water flow WF, along the outer periphery of the substantially columnar region where the water flow WF is formed, below the measurement region R. Further, the tubular body 48a and the tubular body 48b of the gas guide section 48 configure a shielding portion. The shielding portion is interposed between the recovery port 15a and the photodetector 30 and blocks light such that noise light N2 which is generated at the recovery port 15a does not reach the photodetector 30.

In the particulate measurement device 1, the water W discharged from the opening 11 of the nozzle 10 falls as the substantially columnar water flow WF. The water flow WF maintains a stable column shape in which a turbulent flow is suppressed, in a long section due to the air flow around the water flow WF. Further, in the particulate measurement device 1, the light emitter 20 emits the light LB into the water flow WF. The emitted light LB is propagated downward in the water flow WF while being totally reflected at the interface between the water flow WF and the air. In a case where the particulates P are present in the water flow WF, the light LB propagating in the water flow WF is irradiated to the particulates P. As a result, the scattered light S from the particulate P is generated. If the scattered light S is incident on the interface at an angle smaller than the critical angle, the scattered light S penetrates the interface of the water flow WF. The scattered light S having penetrated the interface of the water flow WF in the measurement region R is detected by the photodetector 30. Then, in the processing unit 33, the number of particulates is measured based on a signal (the intensity of the scattered light S) from the photodetector 30. The water flow WF having passed through the measurement region R flows into the recovery port 15a while maintaining a stable substantially columnar shape due to the air flow AF2 from the air flow forming unit 45.

According to the particulate measurement device 1, as described above, the stable substantially columnar water flow WF is formed over a long section. Therefore, it is possible to lengthen the measurement region R, and thus it is possible to obtain a signal having a high SN ratio based on light from the particulate passing through the measurement region R.

Further, the air flow forming unit 40 has an adjustment function for adjusting the speed of the air flow. Accordingly, the speed of the air flow is adjusted according to the speed of the water flow WF which is discharged from the nozzle 10. Therefore, a more stable substantially columnar water flow WF is formed.

Further, even if the noise light N1 having an angle smaller than the critical angle with respect to the interface of the water flow WF is emitted from the opening 11, the noise light N1 is blocked by the shielding portion, that is, the gas guide section 41. Therefore, noise is reduced. Further, the gas guide section 41 configures the shielding portion, and therefore, a separate component for light shielding is unnecessary.

Further, the light emitter 20 has the condensing lens 23 which narrows the beam width of the light LB in the opening 11 to be smaller than the opening 11. Accordingly, the noise light N1 which is generated due to the light LB from the light emitter 20 being reflected or scattered at the opening end 11a is suppressed. Further, the light condensed by the condensing lens 23 spreads in the water flow WF, and therefore, the light LB propagates in a wide range in the water flow WF.

Further, the particulate measurement device 1 is provided with the recovery part 15 having the recovery port 15a for recovering the water flow WF, and the air flow forming unit 45 which forms the air flow AF2 on the side of the recovery port 15a with respect to the measurement region R and on the outer periphery of the water flow WF. Accordingly, it is possible to stabilize the water flow WF on the side of the recovery port 15a with respect to the measurement region R. Therefore, the noise light N2 which is generated from the side of the recovery port 15a with respect to the measurement region R can be reduced.

Second Embodiment

Figure 3:
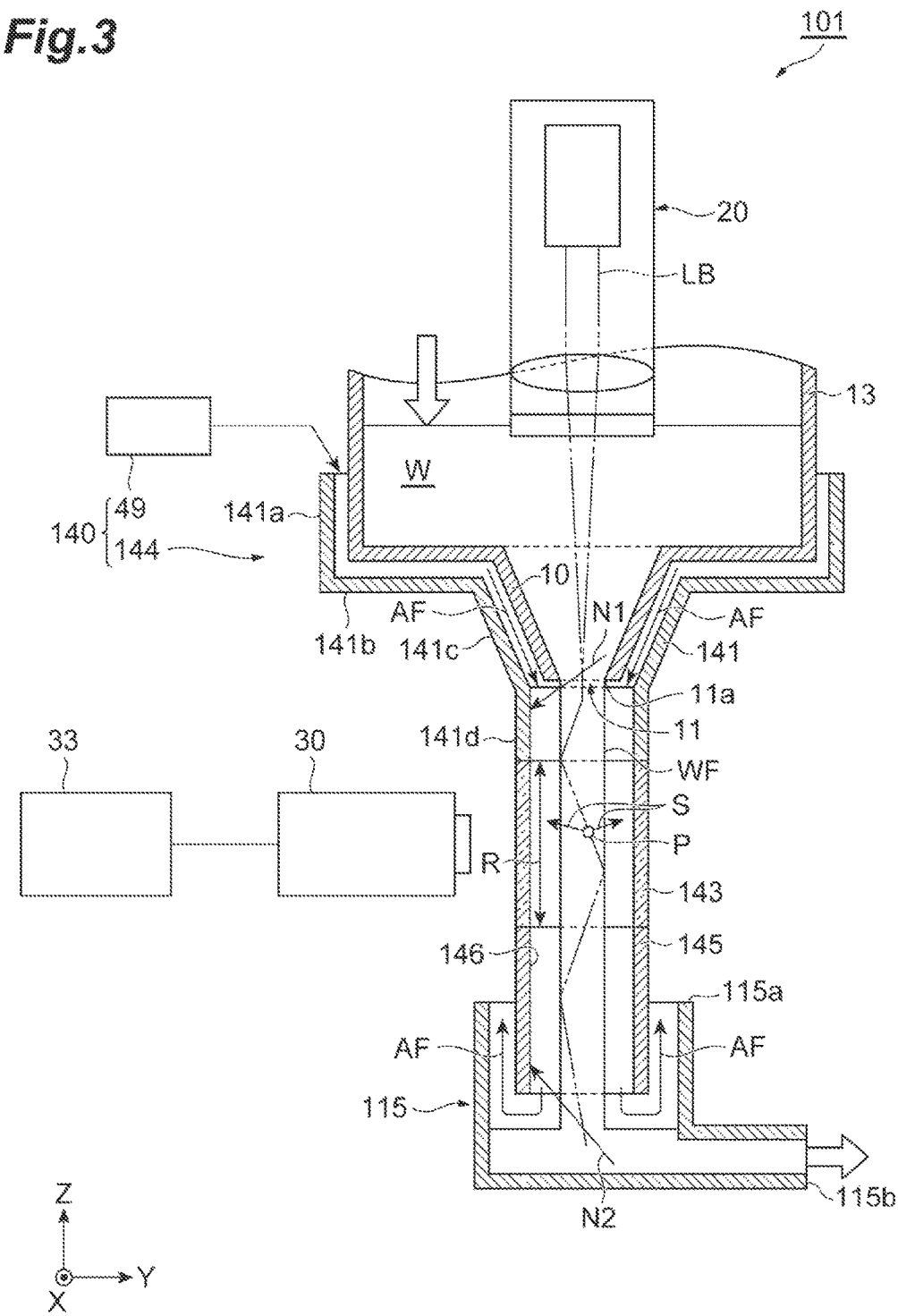
FIG. 3 is a sectional view schematically showing a particulate measurement device according to a second embodiment.

Next, a particulate measurement device according to a second embodiment will be described with reference to FIG. 3. A particulate measurement device 101 shown in FIG. 3 is different from the particulate measurement device 1 of the first embodiment in terms of the configurations of an air flow forming unit 140 and a recovery part 115. Hereinafter, points different from those of the first embodiment will be mainly described. The same elements or members are denoted by the same reference symbols and a detailed description thereof is omitted.

The particulate measurement device 101 is provided with the nozzle 10, the reservoir 13, the light emitter 20, the photodetector 30, the processing unit 33, and the air flow forming unit 140. The air flow forming unit 140 has a gas guide section 144 and the blower 49. The blower 49 is connected to the gas guide section 144.

The gas guide section 144 includes an upper tubular body 141, an intermediate tubular body 143, and a lower tubular body 145. The upper tubular body 141 includes an upper portion 141a, a first intermediate portion 141b, a second intermediate portion 141c, and a lower portion 141d. The upper portion 141a has a cylindrical shape. The first intermediate portion 141b has an annular plate shape extending inward from a lower end of the upper portion 141a. The second intermediate portion 141c is continuous with an inner edge of the first intermediate portion 141b and has a tubular shape which decreases in diameter as it approaches a lower end of the second intermediate portion 141c. The upper portion 141a, the first intermediate portion 141b, and the second intermediate portion 141c extend to surround the reservoir 13 and the nozzle 10, and form a gas flow path from the portions 141a, 141b, and 141c to the reservoir 13 and the nozzle 10. Further, the lower portion 141d has a cylindrical shape, is continuous with the lower end of the second intermediate portion 141c, and extends to a position below the opening 11 of the nozzle 10. Further, the lower portion 141d surrounds the substantially columnar region where the water flow WF is formed, with a space serving as a gas flow path from the lower portion 141d to the substantially columnar region. If gas is supplied from the blower 49 to the upper tubular body 141, the gas flows downward through the space extending from the reservoir 13 and the nozzle 10 to the upper tubular body 141. Further, the upper tubular body 141 has a light shielding property and is interposed between the opening 11 and the photodetector 30 to configure a shielding portion. The shielding portion blocks light such that the noise light N1 which is generated at the opening 11 does not reach the photodetector 30.

The intermediate tubular body 143 is a tubular member having a cylindrical shape which extends downward to be continuous with the lower end of the upper tubular body 141. The intermediate tubular body 143 is formed of an optically transparent material such as quartz glass, for example. The intermediate tubular body 143 surrounds the substantially columnar region where the water flow WF is formed, with a space serving as a gas flow path extending between the intermediate tubular body 143 and the substantially columnar region. An air flow AF formed by the air flow forming unit 140 having the intermediate tubular body 143 passes between the interface of the water flow WF and the inner peripheral surface of the intermediate tubular body 143. The region surrounded by the intermediate tubular body 143, of the region where the water flow WF is formed, is the measurement region R. For this reason, the photodetector 30 is disposed to face the intermediate tubular body 143 so as to be able to observe the scattered light S from the measurement region R.

The lower tubular body 145 is a tubular member having a cylindrical shape which extends downward to be continuous with the lower end of the intermediate tubular body 143. The lower tubular body 145 surrounds the substantially columnar region where the water flow WF is formed, with a space serving as a gas flow path extending between the lower tubular body 145 and the substantially columnar region. The lower end side of the lower tubular body 145 enters the inside of the recovery part 115. A recovery port 115a having a larger diameter than the lower tubular body 145 is formed in an upper portion of the recovery part 115. Further, a drainage port 115b for discharging water is formed in a lower portion of the recovery part 115. Then, the lower end side of the lower tubular body 145 is inserted with a predetermined gap from the inner periphery of the recovery port 115a. The air flow AF formed by the air flow forming unit 140 passes between the interface of the water flow WF and the inner peripheral surface of the lower tubular body 145 and is then discharged from the gap between the lower tubular body 145 and the recovery port 115a to the outside. Further, the lower tubular body 145 has a light shielding property and configures a shielding portion 146. The shielding portion 146 is located between the recovery port 115a and the photodetector 30 and blocks light such that the noise light N2 which is generated at the recovery port 115a does not reach the photodetector 30.

In one embodiment, the gas guide section 144 has the intermediate tubular body 143, and the intermediate tubular body 143 is an optically transparent tubular member and is provided to surround the measurement region R through a region where a gas flow is formed. Accordingly, the air flow AF around the measurement region R is stabilized. Further, the intermediate tubular body 143 configures the gas guide section 144 continuously with the upper tubular body 141 and the lower tubular body 145. That is, the gas guide section 144 is continuously formed in the entire range from the opening 11 of the nozzle 10 to the recovery part 115. In this manner, the air flow AF surrounding the water flow WF over a long distance is formed by the upper tubular body 141, the intermediate tubular body 143, and the lower tubular body 145, and therefore, the water flow WF is more stabilized.

Various embodiments have been described above. However, modifications may be made without being limited to the above-described embodiments. For example, in the embodiments described above, a laser light source is adopted as the light source 21. However, without being limited to laser light source, it is possible to adopt other light sources such as an LED, as the light source 21.

Further, in the embodiments described above, a configuration of detecting the scattered light S when the light LB is irradiated to the particulate P is adopted. However, there is no limitation thereto. For example, the particulate measurement device may have a configuration in which excitation light is emitted from a light emitter to a fluid which includes particulates (for example, bacteria, viruses, or the like) to which a fluorescent label is attached, and fluorescence is detected by a photodetector.

Further, an example is shown in which only one photodetector 30 is provided. However, there is no limitation thereto. For example, in a case where the measurement region R in the water flow WF is lengthened, or the like, a plurality of photodetectors may be provided. By providing a plurality of photodetectors, it is possible to improve the detection sensitivity of the scattered light S or the SN ratio.

Further, an example is shown in which the emission port 26 is disposed to be immersed in the water W in the reservoir 13. However, the emission port may be separated from the water surface.

Further, an example is shown in which the air flow AF2 is generated from the air flow forming unit 45 with the blower 49 connected thereto. However, a suction device may be used instead of the blower 49.

Further, in the respective embodiments, mutual configurations may be appropriately combined. For example, the mirror 35 in the first embodiment may be used in the second embodiment. Further, in addition to the configuration of generating the air flow from the gas guide section 41 in the first embodiment, a blower may be provided such that an air flow is also generated from a space extending from the reservoir 13 and the nozzle 10 to the tubular body 41a, as in the gas guide section 144 in the second embodiment. An air flow does not leak from between the tubular body 41a and the nozzle 10, and a downward air flow can be efficiently generated. Further, a blower may be provided such that an air flow is generated only from a space extending from the reservoir 13 and the nozzle 10 to the tubular body 41a, with the tubular body 41b removed from the gas guide section 41 in the first embodiment.

REFERENCE SIGNS LIST 1, 101: particulate measurement device
10: nozzle
11: opening
20: light emitter
15, 115: recovery part
15a, 115a: recovery port
30: photodetector
40, 45, 140: air flow forming unit
41, 48, 144: gas guide section

The invention claimed is:

1. A particulate measurement device comprising:
a nozzle which discharges liquid containing particulates from an opening thereof to form a flow of the liquid;
a light emitter which emits light such that the light propagates in a first region where the flow of the liquid having a columnar shape is formed;
a photodetector provided outside the first region to receive the light from a second region, the second region being a partial region of the first region and extending along a longitudinal direction of the first region; and
an air flow forming unit including a gas guide section having a tubular body surrounding the first region, the tubular body configured to form a flow of gas along a direction of the flow of the liquid around the first region,
wherein the light emitter emits light from an inside of the nozzle through the opening,
a shielding portion which blocks light is provided between the opening and the photodetector, and
the tubular body of the air flow forming unit is interposed between the opening of the nozzle and the photodetector to configure the shielding portion.

2. The particulate measurement device according to claim 1, wherein the air flow forming unit has an adjustment function for adjusting a speed of the flow of the gas.

3. The particulate measurement device according to claim 1, further comprising:
an optically transparent tubular member provided to surround the second region, a region where the flow of the gas is formed being provided between the optically transparent tubular member and the second region,
wherein the photodetector is disposed to face the optically transparent tubular member.

4. The particulate measurement device according to claim 1, further comprising:
a recovery part having a recovery port for recovering the liquid; and
another air flow forming unit which forms a flow of gas along a direction of the flow of the liquid around the first region, on a side of the recovery port with respect to the second region.

5. The particulate measurement device according to claim 1, wherein the light emitter has a condensing optical element which narrows a beam width of the light in the opening to be smaller than the opening.

6. The particulate measurement device according to claim 1, wherein the gas guide section comprises the tubular body and an other tubular body provided coaxially to surround the first region, a gap between the first tubular body and the second tubular body functions as a gas flow path, and an end of the tubular body and an end of the other tubular body configures a gas discharge port from which the gas guide section discharges the gas to form the flow of the gas around the first region.

7. The particulate measurement device according to claim 1, wherein the tubular body surrounds the nozzle to form a space between the tubular body and the nozzle so that the gas flowing through the space forms the flow of the gas around the first region.

* * * * *